(12) United States Patent
Ambrosius et al.

(10) Patent No.: US 10,894,806 B2
(45) Date of Patent: Jan. 19, 2021

(54) SELECTIVE ENRICHMENT OF ANTIBODIES

(71) Applicants: Dorothee Ambrosius, Laupheim (DE); Michael Dieterle, Biberach an der Riss (DE); Philine Dobberthien, Warthausen (DE); Maria-Katharina Wiegeshoff, Ludwigshafen am Rhein (DE)

(72) Inventors: Dorothee Ambrosius, Laupheim (DE); Michael Dieterle, Biberach an der Riss (DE); Philine Dobberthien, Warthausen (DE); Maria-Katharina Wiegeshoff, Ludwigshafen am Rhein (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 568 days.

(21) Appl. No.: 14/151,949

(22) Filed: Jan. 10, 2014

(65) Prior Publication Data
US 2014/0128578 A1    May 8, 2014

Related U.S. Application Data (63) Continuation of application No. 13/040,361, filed on Mar. 4, 2011, now abandoned.

(30) Foreign Application Priority Data

Mar. 5, 2010    (EP) ...................................... 10155647

(51) Int. Cl.
*C07K 1/32*    (2006.01)
*C07K 14/31*    (2006.01)

(52) U.S. Cl.
CPC ................. *C07K 1/32* (2013.01); *C07K 14/31* (2013.01)

(58) Field of Classification Search
None
See application file for complete search history.

(56) References Cited

U.S. PATENT DOCUMENTS

| | | | |
|---|---|---|---|
| 7,625,764 B2 * | 12/2009 | Stayton | C12N 15/1006 435/283.1 |
| 8,772,447 B2 | 7/2014 | Hall et al. | |
| 2004/0077017 A1 * | 4/2004 | Karlstrom | C40B 30/04 435/7.1 |
| 2006/0121519 A1 | 6/2006 | Patchornik | |
| 2006/0194955 A1 * | 8/2006 | Hober | C07K 16/065 530/388.1 |
| 2007/0072307 A1 | 3/2007 | Godavarti et al. | |
| 2009/0093017 A1 | 4/2009 | Peyser | |
| 2009/0123921 A1 * | 5/2009 | Georgiou | C07K 14/245 435/6.16 |
| 2012/0149875 A1 * | 6/2012 | Johansson | B01D 15/3809 530/387.3 |

FOREIGN PATENT DOCUMENTS

| | | | |
|---|---|---|---|
| EP | 1179014 B1 | 12/2008 | |
| EP | 2157099 A1 | 2/2010 | |
| JP | 0551399 | 8/1991 | |
| JP | 2007244285 A | 9/2007 | |
| WO | 9209633 A1 | 6/1992 | |
| WO | WO 9209633 A1 * | 6/1992 | ............ C07K 14/31 |
| WO | 9506125 | 8/1993 | |
| WO | 2006065208 A1 | 6/2006 | |
| WO | 2006138553 A2 | 12/2006 | |
| WO | WO 2006138553 A2 * | 12/2006 | ........... C07K 16/065 |
| WO | WO 2007019376 A2 * | 2/2007 | ........... A61K 49/085 |
| WO | 2009062942 A2 | 5/2009 | |

OTHER PUBLICATIONS

Nilsson et al. "A synthetic IgG-binding domain based on staphylococcal protein A" Protein Engineering, 1(2), pp. 107-113, 1987.*
Saito et al. "High level expression of a synthetic gene coding for IgG-binding domain B of Staphylococcal protein A" Protein Engineering 2(6), pp. 481-487, published 1989.*
Chen, Jing Ping et al. "Polymer-protein conjugates" Biomaterials (1990) vol. 11, No. 9, pp. 631-634.
Labrou, N. et al. "The Affinity Technology in Downstream Processing" Journal of Biotechnology 36 (1994) pp. 95-119.
Nilsson, Bjorn et al. "A synthetic IgG-binding domain based on staphylococcal protein A" Protein Engineering, (1987) vol. 1, No. 2, pp. 107-113.
International Preliminary Report on Patentability dated Oct. 4, 2012 for PCT/EP2011/053126 filed on Mar. 2, 2011.
Roque, et al., J. Chromatogr. vol. 1160, No. 1-2, p. 44-55, 2007.
Hansson, Lennart et al "Expression of Truncated and Full-Length Forms of Lyme Disease Borrelia Outer Surface Protein A *Escherichia coli*" (1995) Protein Expression and Purification, vol. 6 pp. 15-24.
Löwenadler, Björn et al. "A recombinant *Escherichia coli* heat-stable enterotoxin (STa) fusion protein eliciting anti-STa neutralizing antibodies" (1991) FEMS Microbiology Letters, vol. 82, pp. 271-278.
Bottomley, Stephen P. et al. "Elution of human IgG from affinity columns containing immobilised varients of protein A" (1995) Journal of Immunological Methods, 182, 185-192.
Ljungquist, Charlotta et al. "Thiol-directed immobilization of recombinant IgG-binding receptors" (1989) Eur. J. Biochem. 186, 557-561.

(Continued)

*Primary Examiner* — Daniel E Kolker
*Assistant Examiner* — James L Rogers
(74) *Attorney, Agent, or Firm* — Atabak R. Royaee (57) ABSTRACT

The invention relates to a process for the selective concentration of immunoglobulins or other proteins that contain an Fc domain (target protein), comprising the following steps:
a. preparing a solution that contains the target protein;
b. incorporating an Fc-binding protein with precisely two binding sites under conditions that allow binding to occur;
c. separating the precipitate from the liquid phase;
d. undoing the binding of the target protein from the Fc-binding protein.

6 Claims, 4 Drawing Sheets

Specification includes a Sequence Listing.

(56) References Cited

OTHER PUBLICATIONS

Garret-Flaudy, Frederic et al. "Use of the Avidin (Imino)biotin System as a General Approach to Affinity Precipitation" (2000) Biotechnology and Bioengineering, vol. 71, No. 3, 223-234.
Hilbrig, Frank et al. "Protein purification by affinity precipitation" (2003) Journal of Chromatography, vol. 790, 79-90.
Hoffman, Allan S. "Applications of Thermally Reversible Polymers and Hydrogels in Therapeutics and Diagnostics" (1987) Journal of Controlled Release, vol. 6, 297-305.
Hoffman, Allan S. "Intelligent Polymers" Controlled Drug Delivery, Challenges and Strategies, 485-498.
Mattiasson, B. et al. "Affinity precipitation of proteins: design criteria for an efficient polymer" (1998) Journal of Molecular Recognition, vol. 11, 211-216.
Patchornik, Guy et al. "Free Nonimmobilized Ligands as a Tool for Purification of Proteins" (2005) Bioconjugate Chem. vol. 16, 1310-1315.
Tashiro, Mitsuru et al. "High-resolution Solution NMR Structure of the Z Domain of Staphylococcal Protein A" (1997) Journal of Molecular Biology, 272, 573-590.
Vaidya, A.A. et al. "Enhancing Ligand-Protein Binding in Affinity Thermoprecipitation: Elucidation of Spacer Effects" (1999) Biotechnology and Bioengineering, vol. 64, No. 4, 418-425.
Wilchek, Meir et al. "A New Approach for the Isolation of Biologically Active Compounds by Affinity Chromatography: Isolation of Trypsin", (1973) FEBS Letters, vol. 31, No. 1, 149-152.
Yang, Haiou et al. "Purification of human immunoglobulin G via Fc-specific small peptide ligand affinity chromatography" (2009) Journal of Chromatography A, 1216, 910-918.

\* cited by examiner

SELECTIVE ENRICHMENT OF ANTIBODIES

BACKGROUND TO THE INVENTION

Technical Field

The present invention relates to purification processes for proteins, particularly immunoglobulins or other proteins that have an Fc domain.

State of the Art

Biomolecules such as proteins, polynucleotides, polysaccharides and the like are increasingly gaining commercial importance as medicines, as diagnostic agents, as additives in foods, detergents and the like, as research reagents and for many other applications. The need for such biomolecules can no longer normally be met—for example in the case of proteins—by isolating molecules from natural sources, but requires the use of biotechnological production methods.

The biotechnological preparation of proteins typically begins with the cloning of a DNA fragment into a suitable expression vector. After transfection of the expression vector into suitable prokaryotic or eukaryotic expression cells and subsequent selection of transfected cells the latter are cultivated in bioreactors and the desired protein is expressed. Then the cells or the culture supernatant is or are harvested and the protein contained therein is worked up and purified.

In the case of eukaryotic expression systems, i.e. when using mammalian cell cultures such as CHO or NSO cells, for example, there has been a significant increase in the last 15 years in the concentration of the desired protein in the cell cultures or cell culture supernatants that can be achieved in the expression step. Over the same period, the binding capacity of chromatographic materials that are used in the subsequent purification of the proteins increased only slightly, by comparison. For this reason there is a pressing need for improved, optimised purification methods for biomolecules, particularly proteins, that can be carried out on a large industrial scale.

In the case of biopharmaceuticals, such as for example proteins used as drugs, e.g. therapeutic antibodies, the separation of impurities is of major importance, in addition to the product yield. A distinction can be drawn between process- and product-dependent impurities. The process-dependent impurities contain components of the host cells such as proteins (host cell proteins, HCP) and nucleic acids and originate from the cell culture (such as components of the medium) or from the working up (such as for example salts or dissolved chromatography ligands). Product-dependent impurities are molecular variants of the product with different properties. These include shortened forms such as precursors and hydrolytic breakdown products, but also modified forms, produced for example by deaminations, incorrect glycosylations or wrongly linked disulphide bridges. Also included among the product-dependent variants are polymers and aggregates, Other impurities are contaminants. This term covers all other materials of a chemical, biochemical or microbiological nature that do not belong directly to the production process. Examples of contaminants include viruses that may occur in undesirable manner in cell cultures.

In the case of biopharmaceuticals, impurities give rise to safety concerns. These concerns are intensified if, as very often happens with biopharmaceuticals, the therapeutic proteins are administered directly into the bloodstream by injection or infusion. Thus, host cell components may lead to allergic reactions or immunopathological effects. In addition, impurities may also lead to an undesirable immunogenicity of the protein administered, i.e. they may trigger an undesirable immune reaction to the therapeutic agent in the patient, possibly leading to life-threatening anaphylactic shock. Therefore, there is a need for suitable purification processes by means of which all unwanted substances can be reduced to a harmless level.

On the other hand, even in the case of biopharmaceuticals, economic considerations cannot be ignored. Thus, the production and purification methods used should not compromise the economic viability of the biopharmaceutical product thus produced.

As working up and processing steps for proteins, (column) chromatographic processes as well as filtration and precipitation processes are of crucial importance. Thus, the precise operation of concentrating antibodies contains a step of purification by affinity chromatography. Accordingly, numerous methods of column chromatography and the chromatography materials that can be used in these processes are currently known.

Affinity chromatography matrices are used as the stationary phase in the industrial purification of various substances. Immobilised ligands can be used for specifically concentrating and purifying substances that have a certain affinity for the particular ligand used. For the industrial purification of antibodies (immunoglobulins), particularly the purification of monoclonal antibodies, immobilised protein A is often used as the initial purification step. Protein A is a protein with about 41 kDa of *Staphylococcus aureus* that binds with high affinity ($10^{-8}$ M-$10^{-12}$ M of human IgG) to the $CH_2/CH_3$ domain of the Fc region of immunoglobulins. In protein A chromatography, immunoglobulins or fusion proteins that have a protein A-binding Fc region from the mobile phase bind specifically to the protein A ligand, which is covalently coupled to a carrier (e.g. Sepharose). Protein A from *Staphylococcus aureus* (wild-type protein A) and genetically modified recombinant protein A (rec. protein A) interacts through non-covalent interactions with the constant region (Fc fragment) of the antibodies. This specific interaction can be used to separate impurities efficiently from the antibody. By altering the pH, the interaction between the antibody and the protein A ligand can be deliberately stopped and the antibody released or eluted from the stationary phase.

Apart from protein A as affinity ligand, there are many other molecules currently known that bind to the Fc fragment. Thus, individual domains of protein A are used instead of the complete protein (8). Protein variants are known, which differ precisely from the B domain of the protein A, which are suitable for binding Fc-fragment-containing molecules (16, 17). These different variants differ essentially in the mutations that have been inserted in order to increase the stability or binding affinity. These mutants of the B domain are usually known as Z-domain or protein Z. Besides protein A or protein G, various peptides are also suitable for selective binding to the Fc fragment (14). The present great interest in affinity ligands for the Fc fragment lead one to suppose that still more affinity ligands are being found.

Affinity chromatography and particularly the frequently used protein A chromatography are expensive, however, and precisely when there are increasing product concentrations in the fermenter and large quantities of product, there are limits on the chromatographic purification processes that can be carried out. The critical points are: loading capacities, number of cycles, process times, pool volumes and quantities of buffer. In the future, therefore, alternative purification processes will be essential. A general overview of conventional purification strategies, including affinity chromatography and alternative methods of affinity chromatography, can be found in the following articles (7+10).

A more recent method of affinity chromatography uses not a constantly immobilised affinity ligand but, to begin with, a solubilised affinity ligand that is mixed with the target protein (11). The affinity ligand carries a fusion tag or a fusion protein which makes it possible to carry out the immobilisation of the affinity ligand on a solid phase that takes place in the second step. In the next step, as in conventional affinity chromatography, the target protein is separated from the ligand under suitable conditions and thus eluted from the column.

The invention described here uses affinity precipitation instead of affinity chromatography to purify biomolecules. This method appears to have great potential precisely when used on a larger scale (1, 2).

Affinity precipitation is the most effective method of protein precipitation (2). The precipitation of a protein from a solution in general is a well known process that is frequently used. Thus, many proteins have already been separated from a solution by ammonium sulphate precipitation from a protein mixture. During this precipitation, macromolecules (e.g. proteins) are removed from the solution and converted into particles. Depending on the difference in density between the particle and the solution and the particle diameter, this step leads to precipitation. However, this precipitation usually takes place non-specifically.

For more selective concentration of a molecule, e.g. a protein, therefore, affinity precipitation was developed. Affinity precipitation makes use of the selective binding of an affinity molecule to a target molecule. Affinity molecules may be for example proteins, peptides, oligonucleotides or small chemical molecules. A distinction is drawn in affinity precipitation between two principles, first and second order affinity precipitation (7). In first order affinity precipitation, both the affinity molecule and the target molecule have two binding sites, so that it is possible for a network to form between the two molecules and an affinity complex is formed that sediments at a specific size. In second order affinity precipitation, affinity macroligands (AML) are used, for example. In this type of precipitation, the affinity molecule is bound to a stimulatable substance, usually a polymer. The stimulatable substance changes its solubility characteristics as a result of a change in the ambient conditions, such as e.g. a shift in the pH or temperature, and precipitation occurs. Unlike first order affinity precipitation, there is no need for a bifunctional affinity molecule or for a bifunctional target molecule either.

In the affinity precipitation that is mostly used, the affinity ligands are at present coupled to polymers or other mediators (15).

The affinity precipitation of molecules containing Fc fragment has already been described in a number of studies. The most common application at present is characterised by the use of so-called "smart polymers". "Smart polymers" (or stimuli-responsive "intelligent" polymers or affinity macroligands) are polymers that can change their properties in response to external influences (physical or chemical stimuli). These stimuli may be for example changes in pH or temperature (12-13). Usually, smart polymers react to their stimuli with precipitation in solution. This precipitation can be reversed, after the desired separation of the supernatant solution, by suitable conditions. Smart polymers can be conjugated with various biomolecules, leading to a large accumulation of polymer/biomolecule systems that can be used for all kinds of applications. Examples of these biomolecules include proteins, oligonucleotides and sugars.

Another form of affinity precipitation is the recently described "affinity sinking" method. In this form of affinity precipitation, a linking molecular scaffold is used to bind a number of affinity ligands to one another. This then makes it possible to form the network required for precipitation. The binding of the affinity ligand to the network former may take place both non-covalently and covalently. This method was recently described in the patent "Compositions and methods for purifying and crystallizing molecules of interest" (6). In this, first of all a solution containing antibodies is mixed with an affinity ligand that is covalently bound to a crosslinker. No precipitation is observed. Only after the subsequent addition of a coordinating ion or molecule does precipitation take place. In a second similar application the affinity ligand is linked to a biotin-binding protein which forms a network with the mediator avidin (9).

U.S. Pat. No. 7,083,943 describes an affinity precipitation in which a binding domain for the target protein is linked to a scaffold domain the amino acid sequence of which is intended to assist the tendency to precipitation.

Chen and Hoffman (15) describe the affinity precipitation of IgG with poly(N-isopropylacrylamide)-protein A conjugates. The precipitation of antibodies with unmodified protein A, however, has not proved effective.

One disadvantage of the methods described in the prior art is that during first order affinity precipitation, precipitation is possible only via the cross-linking molecule, or in second order affinity precipitation a stimulatable substance is required. Other disadvantages of the affinity precipitations that are best known are on the one hand a) steric hindrance in which the binding of the target protein is limited by the binding of high-molecular affinity macroligands, b) the resolubilisation of the precipitated polymer complex is slow, c) the non-specific co-precipitation of impurities, that generally require a second precipitation step, d) the additional step of binding an affinity protein to the polymer or to the cross-linker (2-5).

BRIEF SUMMARY OF THE INVENTION

The present invention relates to affinity precipitation using a binding protein with two binding sites, which dispenses completely with an additional fusion protein or a linker molecule. The affinity protein on its own is sufficient for the precipitation, and there is no need for a stationary phase. The invention used here also makes it easier to recover the affinity protein.

The invention relates in particular to a process for the selective concentration of immunoglobulins or other proteins that contain an Fc domain (target protein), comprising the following steps:
  a. preparing a solution that contains the target protein;
  b. incorporating an Fc-binding protein with precisely two binding sites under conditions that allow binding to occur;
  c. separating the precipitate from the liquid phase;
  d. undoing the binding of the target protein from the Fc-binding protein.

In another aspect the invention relates to a process in which the Fc-binding protein is a dimer of an Fc-binding domain of protein A or protein G. Preferably, the two monomers of the dimer are linked to one another via a disulphide bridge.

In another aspect the invention relates to a process in which the dimer is a homodimer, the monomers of which have the SEQ ID NO: 1, SEQ ID NO: 2, or SEQ ID NO: 3 or a sequence that differs from SEQ ID NO. 1 in 1, 2, 3, 4, 5, 6, 7, 8, 9, 10, 11, 12, 13, 14, 15, 16, 17, 18, 19 or 20 amino acids.

In another aspect the Fc-binding protein is used in a ratio of 0.5-20 in relation to the target protein. The solution in step a. preferably has a pH of 5.5-8. Preferably, the undoing of the binding in step d. takes place at a pH of 2-4.5.

In another aspect the invention relates to an Fc-binding protein consisting of 2 identical sub-units that have the sequence SEQ ID NO: 1, SEQ ID NO: 2, SEQ ID NO: 3, or a sequence that differs from SEQ ID NO. 1 in 1, 2, 3, 4, 5, 6, 7, 8, 9, 10, 11, 12, 13, 14, 15, 16, 17, 18, 19 or 20 amino acids, the two sub-units being linked to each other via a covalent bond. Preferably, the covalent bond is a disulphide bond.

BRIEF DESCRIPTION OF THE FIGURES

FIG. 1: SDS-PAGE of the Z dimer. To demonstrate the dimerisation via cysteines, iodoacetamide or iodoacetamide with dithiothreitol was added before the application to the SDS-PAGE.

| Trace | Sample |
|---|---|
| 1 | recombinant Z-dimer mixed with 0.6 µmol iodoacetamide |
| 2 | recombinant Z-dimer mixed with 0.3 µmol DTT and iodoacetamide |
| 3 | pure recombinant Z-dimer |
| 4 | Kombi marker |
| 5 | recombinant Z-dimer mixed with 0.2 µmol iodoacetamide |
| 6 | recombinant Z-dimer mixed with 0.1 µmol DTT and 0.2 µmol iodoacetamide |
| 7 | pure recombinant Z-dimer |

| Trace | Sample |
|---|---|
| 1 | purified antibody |
| 2 | protein Z dimer |
| 3 | supernatant after precipitation |
| 4 | supernatant after an optional washing step |
| 5 | resuspended pellet (antibody with Z-dimer) |
| 6 | peak 1 of the ion exchange chromatography at an acid pH (antibody) |
| 7 | peak 2 of the acid ion exchange chromatography at an acid pH (Z-dimer) |
| 8 | Kombi marker |

DETAILED DESCRIPTION OF THE INVENTION

The present invention relates to methods of depleting impurities, particularly host cell protein (HCP) and DNA, from protein compositions of the kind obtained from cell cultures in which proteins are expressed recombinantly or endogenously. In particular, the invention relates to methods of purifying or concentrating a protein (target protein) by binding an Fc-binding protein or multimer thereof with at least two binding sites. In further steps the precipitate is separated off and then the binding of the Fc-binding protein to the target protein is removed using suitable conditions.

The present invention relates to a process for the selective concentration of immunoglobulins or other proteins that contain an Fc domain (target protein), comprising the following steps:

a. preparing a solution that contains the target protein;
b. incorporating an Fc-binding protein with precisely two binding sites under conditions that allow binding to occur;
c. separating the precipitate from the liquid phase;
d. undoing the binding of the target protein from the Fc-binding protein.

The target protein may be in particular an immunoglobulin or a protein that contains the Fc domain of an immunoglobulin and can bind to protein A or fragments of protein A.

Immunoglobulins consist of two heavy and two light chains. The heavy chains each have one variable and three to four constant domains depending on the immunoglobulin. These are referred to analogously as VH and CH1, CH2, CH3. The variable domains of a light and a heavy chain form the antigen binding site. The domain CH2 contains a carbohydrate chain which forms a binding site for the complement system. The CH3 domain contains the Fc-receptor binding site. Target proteins to which the process according to the invention can be applied are all proteins that have an Fc domain. Examples of proteins that contain CH2/CH3 regions are antibodies, immunoadhesins and fusion proteins in which the protein of interest is connected to a CH2/CH3 region. In one embodiment of the invention, the target protein is for example an antibody that has a CH2/CH3 region and is thus capable of binding to protein A. The term CH2/CH3 region refers to the amino acids in the Fc region of an antibody that interact with protein A.

The Fc-binding protein comprises according to the invention precisely two binding sites for one Fc domain.

In another aspect the invention relates to a process wherein the Fc-binding protein is a dimer of an Fc-binding domain of protein A or protein G. The two monomers of the dimer are preferably linked together by a disulphide bridge.

By an Fc-binding protein are meant proteins or peptides which are capable of binding to the Fc region. Preferably, Fc-binding proteins bind with a dissociation constant ($K_D$ value) in the range from $10^{-2}$-$10^{-13}$M.

In preferred embodiments of the invention the Fc-binding protein is a homo- or heterodimer of Fc-binding domains which comprise or contain the sequences listed in Table 1:

| SEQ ID NO: | Sequence | Description |
|---|---|---|
| 1 | MVDNKFNKEQ QNAFYEILHL PNLNEEQRNA FIQSLKDDPS QSANLLAEAK KLNDAQAPKS SACRRRRRRR RP | Z-domain Cys tag |
| 2 | MVDNKFNKEQ QNAFYEILHL PNLNEEQRNA FIQSLKDDPS QSANLLAEAK KLNDAQAPKS SAC | Z-domain Cys |
| 3 | DNKFNKEQQN AFYEILHLPN LNEEQRNAFI QSLKDDPSQS ANLLAEAKKL NDAQAPK | Z-domain |
| 4 | QQNAFYQVLN MPNLNADQRN GFIQSLKDDP SQSANVLGEA QKLNDSQAPK | E domain of protein A (Swissprot P02967) |
| 5 | QNNFNKDQQS AFYEILNMPN LNEAQRNGFI QSLKDDPSQS TNVLGEAKKL NESQAPK | D domain of protein A (Swissprot P02967) |
| 6 | DNNFNKEQQN AFYEILNMPN LNEEQRNGFI QSLKDDPSQS ANLLSEAKKL NESQAPK | C domain of protein A (Swissprot P02967) |
| 7 | DNKFNKEQQN AFYEILHLPN LNEEQRNGFI QSLKDDPSQS ANLLAEAKKL NDAQAPK | B domain of protein A (Swissprot P02967) |
| 8 | DNKFNKEQQN AFYEILHLPN LTEEQRNGFI QSLKDDPSVS KEILAEAKKL NDAQAPK | A domain of protein A (Swissprot P02967) |
| 9 | TTYKLVINGK TLKGETTTKT VDAETAEKAF KQYANDNGVD GVWTYDDATK TFTVT | protein G Fc-binding domain from *Streptococcus* Sp. (Uniprot Q53337) |
| 10 | TTYKLVINGK TLKGETTTKA VDAETAEKAF KQYANDNGVD GVWTYDDATK TFTVT | protein G Fc-binding domain from *Streptococcus dysgalactiae* (YP_002997067) |
| 11 | TTYRLVIKGV TFSGETATKA VDAATAEQTF RQYANDNGIT GEWAYDTATK TFTVTE | IgG binding domain from *Streptococcus equi* (YP_002123072) |

By a homodimer is meant, in this context, an Fc-binding protein that is made up of two sub-units of the same sequence.

By a heterodimer is meant, in this context, an Fc-binding protein that is made up of two sub-units of different sequences, each of which has a binding site for an Fc domain. Preferably, the sub-units contain sequences that are selected from the sequences in Table 1.

In another aspect, the invention relates to a process in which the dimer is a homodimer the monomers of which have SEQ ID NO: 1, SEQ ID NO: 2 or SEQ ID NO: 3 or a sequence that differs from SEQ ID NO. 1 in 1, 2, 3, 4, 5, 6, 7, 8, 9, 10, 11, 12, 13, 14, 15, 16, 17, 18, 19 or 20 amino acids. The monomers that differ from SEQ ID NO. 1 in 1, 2, 3, 4, 5, 6, 7, 8, 9, 10, 11, 12, 13, 14, 15, 16, 17, 18, 19 or 20 amino acids have the property of binding Fc-domains with a $K_D$ value in the range from $10^{-2}$-$10^{-13}$M.

Binding conditions are conditions in which binding to the target protein by the Fc-binding proteins takes place, preferably in a pH range of pH 5.5-9, preferably 6-8.

The precipitation occurs spontaneously under binding conditions, such as those found for example in cell-free eukaryotic culture supernatant. There is no need to link the dimers according to the invention to polymers, e.g. polyethyleneglycols, in order to promote precipitation with polymers.

In another aspect the Fc-binding protein is used in a molar ratio of 0.5-20 relative to the target protein.

The separation of the precipitate may be carried out by centrifugation and subsequent removal of the supernatant, but also by filtration techniques.

The undoing of the binding to the target protein is carried out under conditions that enable the Fc-binding protein to be separated from the target protein. Preferably, this can be done by adjusting the pH to a range between pH 2 and 4.5.

In another aspect the invention relates to an Fc-binding protein that consists of 2 identical sub-units that have the sequence SEQ ID NO: 1, SEQ ID NO: 2, SEQ ID NO: 3, or a sequence that differs from SEQ ID NO. 1 in 1, 2, 3, 4, 5, 6, 7, 8, 9, 10, 11, 12, 13, 14, 15, 16, 17, 18, 19 or 20 amino acids, wherein the two sub-units are linked together by a covalent bond. Preferably, the covalent bond is a disulphide bond.

EXAMPLES

Equipment and Methods:
Preparation of the Dimerised Protein Z
Protein Z was obtained as a recombinant protein from *E. coli*. The removal of impurities was carried out after separation of the cell debris by ion exchange chromatography.
Protein sequence of the Z domain used:

(SEQ ID NO: 1)
Met-Val-Asp-Asn-Lys-Phe-Asn-Lys-Glu-Gln-Gln-Asn-Ala-Phe-Tyr-Glu-Ile-Leu-His-Leu-

Pro-Asn-Leu-Asn-Glu-Glu-Gln-Arg-Asn-Ala-Phe-Ile-Gln-Ser-Leu-Lys-Asp-Asp-Pro-Ser-

Gln-Ser-Ala-Asn-Leu-Leu-Ala-Glu-Ala-Lys-Lys-Leu-Asn-Asp-Ala-Gln-Ala-Pro-Lys-Ser-

Ser-Ala-Cys-Arg-Arg-Arg-Arg-Arg-Arg-Arg-Pro

By inserting a non-native cysteine into the peptide chain of the Z domain it is possible to deliberately connect two protein Z molecules via a disulphide bridge. Directly after the purification of the recombinant protein Z the latter is obtained by oxidation as a dimerised protein.

Cell-Free Eukaryotic Culture Supernatant

The cell culture supernatant of CHO cells optimised to secretory production was obtained by filtration or centrifugation after several days' culture.

SEC Analysis

The analysis of protein impurities and the antibody content of the samples from Experiment 1 was carried out by analytical size exclusion chromatography (SEC). A TSK-GEL SW 3000 was used with the precolumn recommended by the manufacturer (TOSOH Bioscience). Analysis was carried out on a Dionex Ultimate apparatus with monitoring of the UV signal at 280 and 220 nm.

Ion Exchange Chromatography for Separating the Z-Dimer from the Antibody

The ion exchange chromatography was carried out on an ÄKTA Explorer 10 apparatus (GE Healthcare) with observation of the UV absorption at 220 and 280 nm. The column material used was SP Sepharose FF (19 mL gel bed volume). After the application of the pellet resuspended at an acid pH, the column was equilibrated with 20 mM phosphate buffer at pH 3.3 and then the antibody and the Z-dimer were separated from one another over a 25 column volume long gradient. A 20 mM phosphate buffer with 3 M NaCl at pH 3.3 was used for the elution.

Protein A HPLC

Protein A HPLC on a Waters or Dionex apparatus (injector pumps and column oven W2790/5, UV detector W2489) was used to determine the antibody content of cell culture-free supernatant and purified antibody. The antibody content of the solutions was determined using the UV signal of the acidically eluting peak.

Concentration

The solutions obtained in the tests were partly concentrated for the analytical methods (Amicon Ultra, exclusion size 3 kD).

SDS-PAGE:

A 20% homogeneous SDS gel was used to test the individual fractions and supernatants. The protein bands were detected by silver staining according to Heukeshoven.

Host Cell Protein Analysis by ELISA Assay

In Experiment 3 the host cell protein analysis was carried out using an ELISA assay.

DNA Analysis

The DNA analysis was carried out after single strand production by an enzymatically catalysed detecting reaction.

UF/DF

A 50 kDa Centramate Sheet PES (polyethersulphone) made by Messrs Pall with a surface area of 180 cm$^2$ was used for the UF/DF tests in Experiment 3. The UF/DF was carried out so that the antibody was initially concentrated six-fold and then diafiltered (exchanged for 6 volumes of the buffer) before being circulated for 10 min with the retentate valve fully open. The diafiltration was repeated twice. The total UF/DF was carried out with 50 mM acetate buffer+100 mM arginine+150 mM NaCl pH 3.0.

Hydrophobic Interaction Chromatography (HIC)

The hydrophobic interaction chromatography (Experiment 3) was carried out with a 27 mL column on an ÄKTA apparatus. The column material used was Toyopearl Phenyl 650 M made by Tosoh. For this purpose, after the UF/DF, 3.5 M ammonium sulphate buffer was added to the retentate until a conductivity of 165 mS/cm was obtained. The column equilibrated with buffer (50 mM acetate+1.2 M ammonium sulphate pH 4) was charged with the retentate from the UF/DF and then a gradient was run over 40 bed volumes to the buffer 50 mM acetate, pH 4.

Experiments

Detecting the Dimerisation of Protein Z by Cysteine

Figure 1:
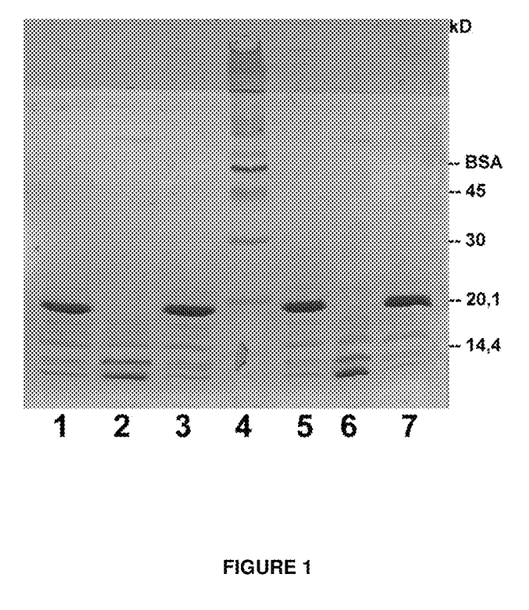

Detection of the dimerisation of protein Z by cysteine was carried out by SDS-PAGE analysis (FIG. 1). To ensure that the working up does not induce any oxidation of the protein Z, first of all the free cysteine groups were alkylated with iodoacetamide. For detecting the monomer, additionally reduction was carried out with dithiothreitol (DTT). 2.6 nmol of Z-dimer were mixed with DTT or a corresponding volume of buffer and incubated for five minutes at 95° C. Then the mixture was cooled to ambient temperature and iodoacetamide or a corresponding volume of buffer was added and the mixture was incubated for a further 20 min in the dark. After five minutes' incubation with SDS-PAGE buffer the preparation was applied to the SDS-PAGE.

The SDS-PAGE analysis shows that the Z monomer is formed by the addition of the reducing agent DTT and the gel band of the Z dimer disappears.

Selective Precipitation using a Z-Dimer

Figure 2:
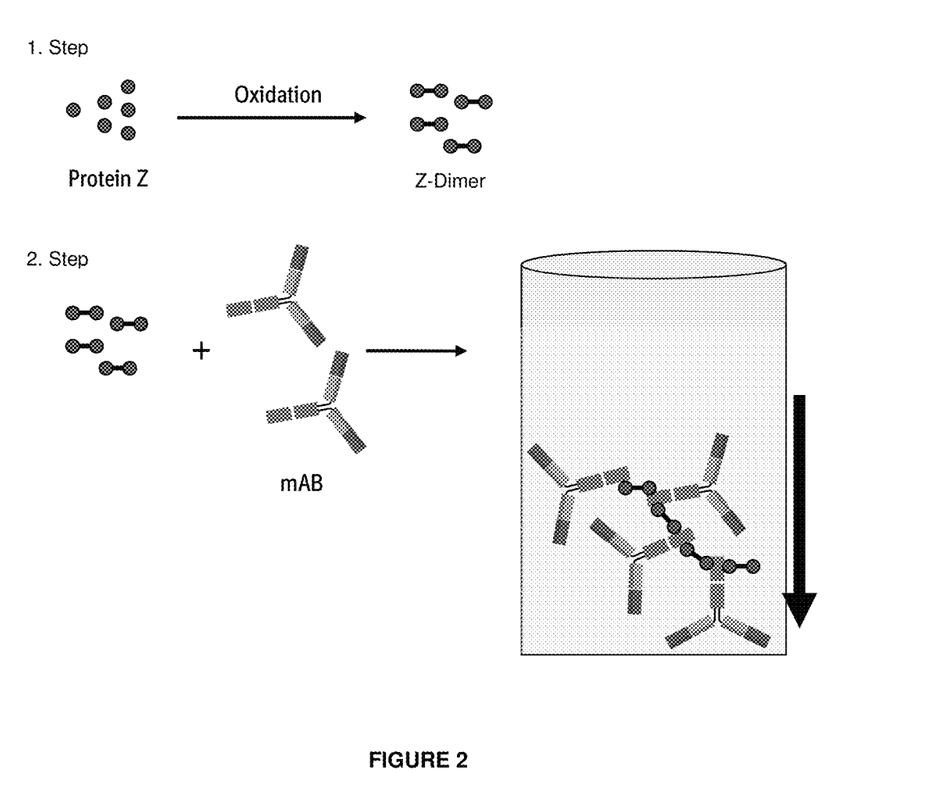
FIG. 2: Affinity precipitation using Z-dimer. As the first step, protein Z is oxidised. In the second step the Z-dimer is added to a solution containing antibody (mAB), which leads to the selective precipitation of the antibody.

The tests described below show that the selective precipitation of an antibody can be achieved with a Z-dimer (FIG. 2, Experiment 1). The Z-dimer is the dimerised B-domain of protein A from *Staphylococcus aureus* linked via two non-native cysteines, which carries a mutation compared with the wild-type (cf. Equipment and Methods). Moreover, Experiment 2 demonstrates that the pellet obtained can be put back into solution by resuspension in the acid pH range and then an antibody can be removed again from the Z-dimer by ion exchange chromatography at an acid pH.

Experiment 1

Different ratios of protein Z to antibody that was present in cell-free eukaryotic culture supernatant were tested. In addition, the volume of the individual batches was varied. In test 1, 0.13 μmol of Z-dimer were incubated, with shaking, with 0.065 μmol of IgG4 contained in cell-free eukaryotic culture supernatant in a total volume of 5.47 mL for 2 h. In test 2, 16.25 nmol of Z-dimer were incubated, with shaking, with 16.25 nmol IgG1 contained in cell-free eukaryotic culture supernatant in a total volume of 5.2 mL, again for 2 h. Then the mixture was centrifuged for 10 min at 4000 rpm and the supernatant was separated from the pellet. The antibody content of the supernatant was determined by means of the UV signal of analytical SEC and by protein A chromatography (Equipment and Methods). The content of antibody in the pellet was determined by subtracting the antibody content of the supernatant from the total content of antibody used. A precipitation of up to 99% antibody was observed (test 1: 99%/test 2: 76%). Moreover, the culture supernatant was examined for protein impurities before and after the precipitation by analytical SEC. The chromatogram from the cell-free eukaryotic culture supernatant was compared directly with the supernatant after precipitation. Depletions of protein impurities ranging from 90-99% were observed (test 1 90%/test 2 99%). This means that 1% or 10% of the protein impurities had been co-precipitated. Protein impurities here may be both host cell proteins and fragments or aggregates of the target protein.

Experiment 2

Figure 3:
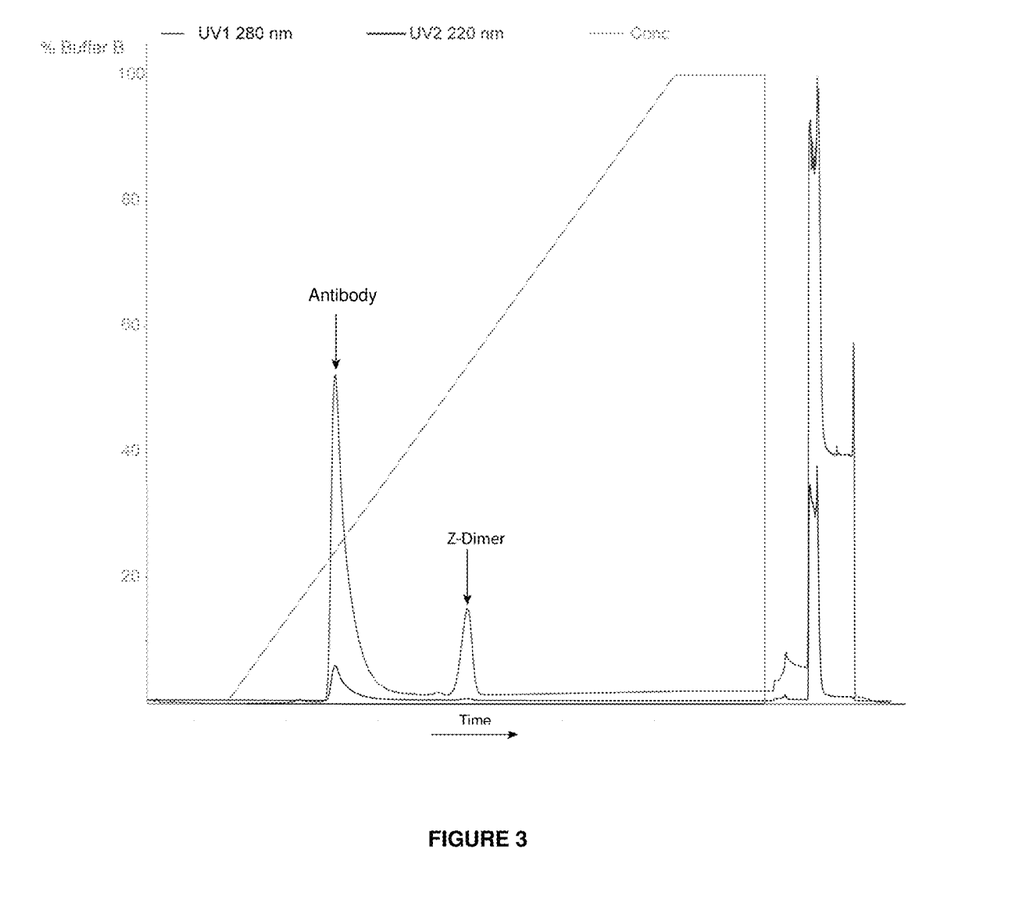
FIG. 3: UV diagram of ion exchange chromatography under acid conditions for separating the Z dimer from the antibody (Experiment 2). The UV chromatogram at 220 nm is shown in red, the UV chromatogram at 280 nm is shown in blue and the increasing content of buffer B (20 mM phosphate, 3 M NaCl) is shown in green.
Figure 4:
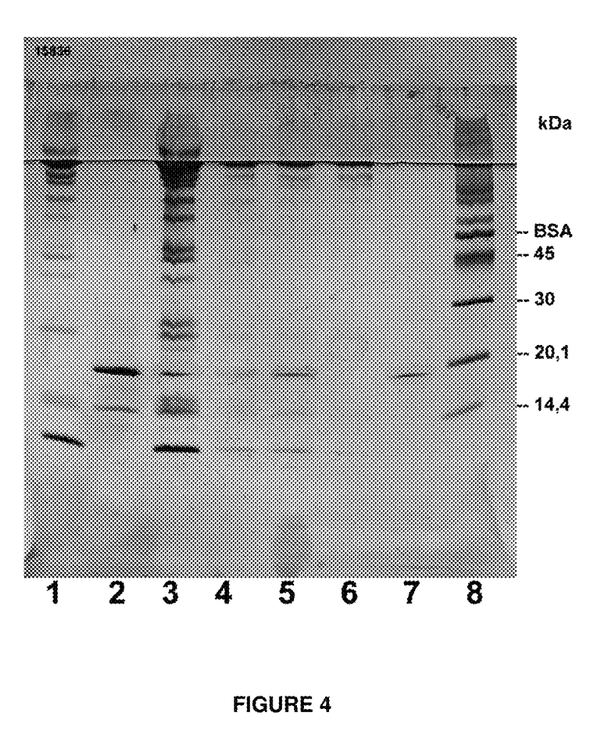
FIG. 4: SDS-PAGE for Experiment 2.

A cation exchanger (SP Sepharose FF) was used to separate the Z-dimer from the antibody. 0.2 μmol of purified antibody were incubated with 0.2 μmol of Z-dimer in a volume of 10.1 mL for 36 min. After subsequent centrifugation (4000 rpm, 10 min) the supernatant was removed. Then the pellet was dissolved batchwise in 10 mL phosphate buffer at pH 7.4 and centrifuged again (4000 rpm, 10 min). The pellet thus obtained was resuspended in 20 mL phosphate buffer (20 mM phosphate, pH 3.3) and purified using an ion exchanger. The Z-dimer could be separated from the antibody through a gradient over 25 bed volumes (FIGS. 3 and 4).

Experiment 3

A multi-step antibody purification process was carried out with affinity precipitation as the capture step.

500 mg of antibody (3.3 μmol) were used in a ratio of 1:2 to Z-dimer (6.6 μmol) in the precipitation from cell-free culture supernatant. After one hour's incubation with gentle agitation, the entire suspension was added to a 0.22 μm filter (Millipore) and in this way the supernatant of the precipitate was separated by filtration. The precipitate was then washed with buffer (231 mL of 50 mM phosphate buffer, pH 7.4) and in the next step resuspended in the filter with acetate buffer (179 mL 50 mM acetate buffer+100 mM arginine+150 mM NaCl pH 3.0). To separate the Z-dimer from the antibody, UF/DF was carried out with a 50 kDa membrane. The next step was HIC to separate off the Z-dimer and further impurities.

The total yield of the antibody was 98% after the precipitation and decreased to 87% after UF/DF and to 64% after HIC. In addition to the good yields obtained with the selective precipitation of the antibody, DNA and host cell protein analysis showed that the DNA could be reduced by 99% by the precipitation step followed by UF/DF and the host cell protein content could be reduced by 99.9% compared with the initial value (cell-free culture supernatant).

LITERATURE

1) Labrou N, Clonis Y D. (1994) *J Biotechnol.* 36(2), 95-119.
2) Hilbrig F, Freitag R. (2003) *J Chromatogr B Analyt Technol Biomed Life Sci.* 790(1-2), 79-90.
3) Mattiasson B, Kumar A, Galaev I Yu. (1998) *J Mol Recognit.* 11(1-6), 211-6.
4) Vaidya A A, Lele B S, Kulkarni M G, Mashelkar R A. (1999) *Biotechnol Bioeng.* 64(4), 418-25.
5) Garret-Flaudy F, Freitag R. (2000-2001) *Biotechnol Bioeng.* 71(3), 223-34.
6) US 2006/0121519 A1 "Compositions and Methods for purifying and crystallizing molecules of interest"
7) H. Chmiel, Bioprozesstechnik, Spektrum Akademischer Verlag, 2nd edition 2006
8) EP1179014B1
9) Patchornik, G. and Albeck A. (2005), *Bioconjugate Chem.* 16, 1310-1315.
10) Wilchek, M. and Gorecki, M. (1973), *FEBS Letters.* 31, 1, 149-152.
11) WO2009062942 KYHSE-ANDERSEN JAN [DK] "DUAL AFFINITY POLYPEPTIDES FOR PURIFICATION"
12) Hoffman, Controlled release (1987) 6, 297-305.
13) Hoffmann (1997) Intelligent polymers. In: Park K, ed. Controlled drug delivery. Washington: *ACS Publications* 485-98.
14) Haiou Yang, Patrick V. Gurgel and Ruben G. Carbonell (2009) *Journal of Chromatography A* 1216, 910-918.
15) Chen and Hoffman (1990), Biomaterials 11 (9), 631-634.
16) Nilsson et al 1987. B. Nilsson, T. Moks, B. Jansson, L. Abrahmsen, A. Elmblad, E. Holmgren, C. Henrichson, T. A. Jones and M. Uhlén, A synthetic IgG-binding domain based on staphylococcal protein A. protein Eng. 1 (1987), pp. 107-113
17) Tashiro, M., Tejero, R., Zimmerman, D. E., Celda, B., Nilsson, B., and Montelione, G. T. 1997. High-resolution solution NMR structure of the Z domain of staphylococcal protein A. J. Mol. Biol. 272: 573-590.

The invention claimed is:

1. Process for the selective concentration of a target protein which is an immunoglobulin or another protein containing an Fc domain, comprising the following steps:
   a. preparing a solution that contains the target protein;
   b. incorporating an Fc-binding protein with precisely two binding sites under conditions that allow binding to occur;
   c. separating precipitate from liquid phase;
   d. separating the Fc-binding protein from the target protein;
   wherein the Fc-binding protein is a dimer of an Fc-binding domain that comprises one of the sequences represented by SEQ ID NO:1 to SEQ ID NO:11, wherein the Fc-binding protein is not conjugated to a polymer, and wherein the Fc-binding protein is not conjugated to protein A.

2. The process according to claim 1, wherein monomers of the dimer are linked together by a disulphide bridge.

3. The process according to claim 1, wherein the Fc-binding protein is used in a molar ratio of 0.5-20 in relation to the target protein.

4. The process according to claim 1, wherein the solution in step a. has a pH of 5.5-9.

5. The process according to claim 4, wherein the solution in step a. has a pH of 6-8.

6. The process according to claim 1, wherein the separating in step d. takes place at a pH of 2-4.5.

* * * * *

SEQUENCE LISTING

<160> NUMBER OF SEQ ID NOS: 11

<210> SEQ ID NO 1
<211> LENGTH: 72
<212> TYPE: PRT
<213> ORGANISM: Staphylococcus aureus

<400> SEQUENCE: 1

Met Val Asp Asn Lys Phe Asn Lys Glu Gln Gln Asn Ala Phe Tyr Glu
1               5                   10                  15

Ile Leu His Leu Pro Asn Leu Asn Glu Glu Gln Arg Asn Ala Phe Ile
                20                  25                  30

Gln Ser Leu Lys Asp Asp Pro Ser Gln Ser Ala Asn Leu Leu Ala Glu
            35                  40                  45

Ala Lys Lys Leu Asn Asp Ala Gln Ala Pro Lys Ser Ser Ala Cys Arg
    50                  55                  60

Arg Arg Arg Arg Arg Arg Pro
65                  70

<210> SEQ ID NO 2
<211> LENGTH: 63
<212> TYPE: PRT
<213> ORGANISM: Staphylococcus aureus

<400> SEQUENCE: 2

Met Val Asp Asn Lys Phe Asn Lys Glu Gln Gln Asn Ala Phe Tyr Glu
1               5                   10                  15

Ile Leu His Leu Pro Asn Leu Asn Glu Glu Gln Arg Asn Ala Phe Ile
                20                  25                  30

Gln Ser Leu Lys Asp Asp Pro Ser Gln Ser Ala Asn Leu Leu Ala Glu
            35                  40                  45

Ala Lys Lys Leu Asn Asp Ala Gln Ala Pro Lys Ser Ser Ala Cys
    50                  55                  60

<210> SEQ ID NO 3
<211> LENGTH: 57
<212> TYPE: PRT
<213> ORGANISM: Staphylococcus aureus

<400> SEQUENCE: 3

Asp Asn Lys Phe Asn Lys Glu Gln Gln Asn Ala Phe Tyr Glu Ile Leu
1               5                   10                  15

His Leu Pro Asn Leu Asn Glu Glu Gln Arg Asn Ala Phe Ile Gln Ser
                20                  25                  30

Leu Lys Asp Asp Pro Ser Gln Ser Ala Asn Leu Leu Ala Glu Ala Lys
            35                  40                  45

Lys Leu Asn Asp Ala Gln Ala Pro Lys
    50                  55

<210> SEQ ID NO 4
<211> LENGTH: 50
<212> TYPE: PRT
<213> ORGANISM: Staphylococcus aureus

<400> SEQUENCE: 4

Gln Gln Asn Ala Phe Tyr Gln Val Leu Asn Met Pro Asn Leu Asn Ala
1               5                   10                  15

Asp Gln Arg Asn Gly Phe Ile Gln Ser Leu Lys Asp Asp Pro Ser Gln
                20                  25                  30

Ser Ala Asn Val Leu Gly Glu Ala Gln Lys Leu Asn Asp Ser Gln Ala
            35                  40                  45

Pro Lys
    50

<210> SEQ ID NO 5
<211> LENGTH: 57
<212> TYPE: PRT

<213> ORGANISM: Staphylococcus aureus

<400> SEQUENCE: 5

Gln Asn Asn Phe Asn Lys Asp Gln Gln Ser Ala Phe Tyr Glu Ile Leu
1               5                   10                  15

Asn Met Pro Asn Leu Asn Glu Ala Gln Arg Asn Gly Phe Ile Gln Ser
            20                  25                  30

Leu Lys Asp Asp Pro Ser Gln Ser Thr Asn Val Leu Gly Glu Ala Lys
        35                  40                  45

Lys Leu Asn Glu Ser Gln Ala Pro Lys
    50                  55

<210> SEQ ID NO 6
<211> LENGTH: 57
<212> TYPE: PRT
<213> ORGANISM: Staphylococcus aureus

<400> SEQUENCE: 6

Asp Asn Asn Phe Asn Lys Glu Gln Gln Asn Ala Phe Tyr Glu Ile Leu
1               5                   10                  15

Asn Met Pro Asn Leu Asn Glu Glu Gln Arg Asn Gly Phe Ile Gln Ser
            20                  25                  30

Leu Lys Asp Asp Pro Ser Gln Ser Ala Asn Leu Leu Ser Glu Ala Lys
        35                  40                  45

Lys Leu Asn Glu Ser Gln Ala Pro Lys
    50                  55

<210> SEQ ID NO 7
<211> LENGTH: 57
<212> TYPE: PRT
<213> ORGANISM: Staphylococcus aureus

<400> SEQUENCE: 7

Asp Asn Lys Phe Asn Lys Glu Gln Gln Asn Ala Phe Tyr Glu Ile Leu
1               5                   10                  15

His Leu Pro Asn Leu Asn Glu Glu Gln Arg Asn Gly Phe Ile Gln Ser
            20                  25                  30

Leu Lys Asp Asp Pro Ser Gln Ser Ala Asn Leu Leu Ala Glu Ala Lys
        35                  40                  45

Lys Leu Asn Asp Ala Gln Ala Pro Lys
    50                  55

<210> SEQ ID NO 8
<211> LENGTH: 57
<212> TYPE: PRT
<213> ORGANISM: Staphylococcus aureus

<400> SEQUENCE: 8

Asp Asn Lys Phe Asn Lys Glu Gln Gln Asn Ala Phe Tyr Glu Ile Leu
1               5                   10                  15

His Leu Pro Asn Leu Thr Glu Glu Gln Arg Asn Gly Phe Ile Gln Ser
            20                  25                  30

Leu Lys Asp Asp Pro Ser Val Ser Lys Glu Ile Leu Ala Glu Ala Lys
        35                  40                  45

Lys Leu Asn Asp Ala Gln Ala Pro Lys
    50                  55

<210> SEQ ID NO 9
<211> LENGTH: 55

```
<212> TYPE: PRT
<213> ORGANISM: Streptococcus Sp.

<400> SEQUENCE: 9

Thr Thr Tyr Lys Leu Val Ile Asn Gly Lys Thr Leu Lys Gly Glu Thr
1               5                   10                  15

Thr Thr Lys Thr Val Asp Ala Glu Thr Ala Glu Lys Ala Phe Lys Gln
            20                  25                  30

Tyr Ala Asn Asp Asn Gly Val Asp Gly Val Trp Thr Tyr Asp Asp Ala
            35                  40                  45

Thr Lys Thr Phe Thr Val Thr
    50                  55

<210> SEQ ID NO 10
<211> LENGTH: 55
<212> TYPE: PRT
<213> ORGANISM: Streptococcus dysgalactiae

<400> SEQUENCE: 10

Thr Thr Tyr Lys Leu Val Ile Asn Gly Lys Thr Leu Lys Gly Glu Thr
1               5                   10                  15

Thr Thr Lys Ala Val Asp Ala Glu Thr Ala Glu Lys Ala Phe Lys Gln
            20                  25                  30

Tyr Ala Asn Asp Asn Gly Val Asp Gly Val Trp Thr Tyr Asp Asp Ala
            35                  40                  45

Thr Lys Thr Phe Thr Val Thr
    50                  55

<210> SEQ ID NO 11
<211> LENGTH: 56
<212> TYPE: PRT
<213> ORGANISM: Streptococcus equi

<400> SEQUENCE: 11

Thr Thr Tyr Arg Leu Val Ile Lys Gly Val Thr Phe Ser Gly Glu Thr
1               5                   10                  15

Ala Thr Lys Ala Val Asp Ala Ala Thr Ala Glu Gln Thr Phe Arg Gln
            20                  25                  30

Tyr Ala Asn Asp Asn Gly Ile Thr Gly Glu Trp Ala Tyr Asp Thr Ala
            35                  40                  45

Thr Lys Thr Phe Thr Val Thr Glu
    50                  55
```